(12) United States Patent
Ghouri

(10) Patent No.: US 7,624,029 B1
(45) Date of Patent: Nov. 24, 2009

(54) COMPUTERIZED SYSTEM AND METHOD FOR RAPID DATA ENTRY OF PAST MEDICAL DIAGNOSES

(75) Inventor: Ahmed Ghouri, San Diego, CA (US)

(73) Assignee: Anvita, Inc., San Diego, CA (US)

( * ) Notice: Subject to any disclaimer, the term of this patent is extended or adjusted under 35 U.S.C. 154(b) by 1179 days.

(21) Appl. No.: 10/351,083

(22) Filed: Jan. 23, 2003

Related U.S. Application Data

(60) Provisional application No. 60/388,444, filed on Jun. 12, 2002, now abandoned.

(51) Int. Cl.
*A61B 5/00* (2006.01)
(52) U.S. Cl. .............................. 705/3; 705/2; 434/236; 709/227; 715/201
(58) Field of Classification Search .............. 705/2, 705/3; 434/236; 709/227; 715/201
See application file for complete search history.

(56) References Cited

U.S. PATENT DOCUMENTS

| | | | | |
|---|---|---|---|---|
| 5,277,188 A * | 1/1994 | Selker | .......................... | 600/508 |
| 5,321,804 A * | 6/1994 | Kusaba et al. | ................ | 715/201 |
| 5,508,912 A * | 4/1996 | Schneiderman | ................. | 705/3 |
| 5,660,176 A * | 8/1997 | Iliff | .............................. | 600/300 |
| 5,737,539 A * | 4/1998 | Edelson et al. | .................. | 705/3 |
| 5,833,599 A | 11/1998 | Schrier et al. | | |
| 5,845,255 A * | 12/1998 | Mayaud | .......................... | 705/3 |
| 5,867,821 A | 2/1999 | Ballantyne et al. | | |
| 6,024,699 A * | 2/2000 | Surwit et al. | ................. | 600/300 |
| 6,151,581 A | 11/2000 | Kraftson et al. | | |
| 6,283,761 B1 * | 9/2001 | Joao | ........................... | 434/236 |
| 6,338,039 B1 | 1/2002 | Lonski et al. | | |
| 6,347,329 B1 * | 2/2002 | Evans | ........................... | 709/202 |
| 6,415,295 B1 * | 7/2002 | Feinberg | .................. | 707/104.1 |
| 6,421,650 B1 * | 7/2002 | Goetz et al. | ..................... | 705/3 |
| 6,684,276 B2 * | 1/2004 | Walker et al. | .................. | 710/73 |
| 7,216,084 B2 * | 5/2007 | Brinkman et al. | ............... | 705/2 |
| 7,225,197 B2 * | 5/2007 | Lissar et al. | ................ | 707/102 |

(Continued)

OTHER PUBLICATIONS

Food and Drug Administration, Center for Drug Evaluation and Research/Approved Drug Products with Therapeutic Equivalance Evaluations/Orange Book/Query (Jul. 3, 2001).*

*Primary Examiner*—C. Luke Gilligan
*Assistant Examiner*—Dilek B Cobanoglu
(74) *Attorney, Agent, or Firm*—DLA Piper LLP (US)

(57) ABSTRACT

A system and method for rapid entry of past medical diagnoses allows for development of specific, clinically relevant diagnoses from a simple input medication through use of a developed database that maps an input medication to a specific medical diagnosis through an intermediate indications data set. Input medications are normalized to their generic or chemical name and the normalized medication data is associated to an intermediate diagnosis through a medications indications listing contained in a database. Each medication develops a short list of possible specific and/or macro-diagnoses (indications) consistent with the medications and a selected indication is concept-matched to a specific medical diagnosis in order to develop a proper diagnosis in clinically meaningful terms, from a concept-mapped portion of the database. The concept-mapped portion is developed by grouping medical terms into clinically meaningful groups and developing pointers within those groups between identified diseases and a developed indications taxonomy, itself developed by forming a composite of FDA-approved and non-FDA approved indications with respect to particular normalized medications.

16 Claims, 6 Drawing Sheets

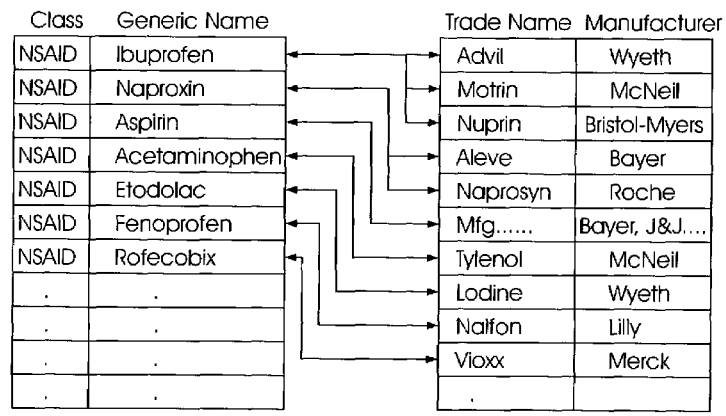

U.S. PATENT DOCUMENTS

| | | |
|---|---|---|
| 2002/0007285 A1* | 1/2002 | Rappaport ..................... 705/2 |
| 2002/0010595 A1 | 1/2002 | Kapp |
| 2002/0019749 A1 | 2/2002 | Becker et al. |
| 2002/0026330 A1 | 2/2002 | Klein |
| 2002/0029223 A1 | 3/2002 | Rice et al. |
| 2002/0032582 A1 | 3/2002 | Feeney et al. |
| 2002/0035484 A1 | 3/2002 | McCormick |
| 2002/0040305 A1 | 4/2002 | Nakatsuchi et al. |
| 2002/0052760 A1 | 5/2002 | Munoz et al. |
| 2002/0091546 A1 | 7/2002 | Christakis et al. |
| 2002/0095313 A1 | 7/2002 | Haq |
| 2002/0116219 A1 | 8/2002 | Ibok et al. |
| 2002/0138621 A1* | 9/2002 | Rutherford et al. .......... 709/227 |
| 2002/0143582 A1 | 10/2002 | Neuman et al. |
| 2002/0147615 A1 | 10/2002 | Doerr et al. |
| 2002/0188466 A1 | 12/2002 | Barrette et al. |
| 2003/0167189 A1* | 9/2003 | Lutgen et al. .................. 705/3 |

* cited by examiner

Search By: All Drugs
Search String: ATE
● Start ○ Anywhere

☐ 0334 Atel
☐ 0334 Atenoblok-Co
☒ 0333 Atenolol
☐ 0334 Atenolol w/Chlorthalidone
☐ 0334 Atenolol:Chlorthalidone
☐ 2135 Atensin Current Drug
ATENOLOL Acute Myocardial Infarction
Angina
Ethanol Withdrawal
Hypertension
Migraine Prophylaxis
Paroxysmal Supraventricular Tachycardia
☒ Unstable Angina
No Indication Found Select Primary Indication

FIG. 1

| Class | Generic Name |
|---|---|
| NSAID | Ibuprofen |
| NSAID | Naproxin |
| NSAID | Aspirin |
| NSAID | Acetaminophen |
| NSAID | Etodolac |
| NSAID | Fenoprofen |
| NSAID | Rofecobix |
| . | . |
| . | . |
| . | . |
| . | . |

| Trade Name | Manufacturer |
|---|---|
| Advil | Wyeth |
| Motrin | McNeil |
| Nuprin | Bristol-Myers |
| Aleve | Bayer |
| Naprosyn | Roche |
| Mfg...... | Bayer, J&J.... |
| Tylenol | McNeil |
| Lodine | Wyeth |
| Nalfon | Lilly |
| Vioxx | Merck |
| . | |

*FIG. 2*

| Select Patient | Demographics | Meds and Dx | Prescriptions | Differential Dx |
|---|---|---|---|---|

Current Patient
AARON, SAMUEL

Past Medical History

| Diagnosis | ICD |
|---|---|
| ACHALASIA | 530.0 |
| ASTHMA | 493.9 |
| CYSTITIS | 595.5 |
| PANIC DISORDER | 300.01 |
| UNSTABLE ANGINA | 411.1 |
| ZINC DEFICIENCY | 985.8 |

Past Surgical History

AXILLO-FEMORAL BYPASS
GASTRECTOMY
ORCHIECTOMY, PARTIAL

| Medication | Indication (Dx) |
|---|---|
| MYOBLOC | ACHALASIA |
| ALBUTEROL | ASTHMA |
| MONISTAT | CYSTITIS |
| CELEXA | PANIC DISORDER |
| ATENOLOL | UNSTABLE ANGINA |

Allergies

| GLIPIZIDE | 5 |
|---|---|

3 Mild
4 Moderate
5 Severe

*FIG. 3*

Search By

All Drugs

Search String

AVA

⦿ Start  ○ Anywhere

☐ 3486  Avalide
☒ 3437  Avandia
☐ 3356  Avapro
☐ 3158  Avaxim

Current Drug

AVANDIA

☒ Diabetes Mellitus
☐ No Indication Found

Select Primary Indication

*FIG. 4*

Current Patient
AARON, SAMUEL

| Select Patient | Demographics | Meds and Dx | Prescriptions | Differential Dx |

Past Medical History
| Diagnosis | ICD |
|---|---|
| ACHALASIA | 530.0 |
| ASTHMA | 493.9 |
| CYSTITIS | 595.5 |
| DIABETES MELLITUS | 000.00 |
| PANIC DISORDER | 300.01 |
| UNSTABLE ANGINA | 411.1 |
| ZINC DEFICIENCY | 985.8 |

Past Surgical History
AXILLO-FEMORAL BYPASS
GASTRECTOMY
ORCHIECTOMY, PARTIAL

| Medication | Indication (Dx) |
|---|---|
| MYOBLOC | ACHALASIA |
| ALBUTEROL | ASTHMA |
| MONISTAT | CYSTITIS |
| CELEXA | PANIC DISORDER |
| ATENOLOL | UNSTABLE ANGINA |
| AVANDIA | DIABETES MELLITUS |

Allergies
| GLIPIZIDE | 5 |

3 Mild
4 Moderate
5 Severe

| Select Patient | Demographics | Meds and Dx | Prescriptions | Differential Dx |

Current Patient
AARON, SAMUEL

Past Medical History
Diagnosis
ACHALASIA
ASTHMA
CYSTITIS
DIABETES MELLITUS
PANIC DISORDER
UNSTABLE ANGINA
ZINC DEFICIENCY Past Surgical History
AXILLO-FEMORAL BYPASS
GASTRECTOMY
ORCHIECTOMY, PARTIAL

| Medication | Indication (Dx) |
|---|---|
| MYOBLOC | ACHALASIA |
| ALBUTEROL | ASTHMA |
| MONISTAT | CYSTITIS |
| CELEXA | PANIC DISORDER |
| ATENOLOL | UNSTABLE ANGINA |
| AVANDIA | DIABETES MELLITUS |

DIABETES MELLITUS

| | Assign ICD and Description to Preliminary Dx |
|---|---|
| 0C0.00 | DIABETES MELLITUS |
| 250 | DIABETES MELLITUS |
| 250.0 | DIABETES MELLITUS - NO COMPLICATION MENTION |
| 250.52 | TYPE II (NON-INSULIN DEPENDENT) OPHTHALMIC MANIF |
| 250.53 | TYPE I (INSULIN DEPENDENT) OPHTHALMIC MANIFESTAT |
| 250.60 | TYPE II (NON INSULIN DEPENDENT) NEUROLOGICAL MA |
| 250.61 | TYPE I (INSULIN DEPENDENT) NEUROLOGICAL MANIFEST |
| 250.70 | TYPE II (NON INSULIN DEPENDENT) PERIPHERAL CIRCU |
| 250.71 | TYPE I (INSULIN DEPENDENT) PERIPHERAL CIRCULATORY |

COMPUTERIZED SYSTEM AND METHOD FOR RAPID DATA ENTRY OF PAST MEDICAL DIAGNOSES

CROSS REFERENCE TO RELATED APPLICATIONS

The present application is related to and takes priority from U.S. provisional patent application entitled Computerized System and Method for Rapid Data Entry of Past Medical Diagnoses, Ser. No. 60/388,444, filed Jun. 12, 2002, and is related to co-pending U.S. patent application entitled System And Method For Patient-Specific Optimization Of Medical Therapy By Simultaneous Symbolic Reasoning In All Clinical Dimensions, filed on instant date herewith, both commonly owned with the present application, the entire contents of both of which are expressly incorporated herein by reference.

FIELD OF THE INVENTION

The present invention relates to systems and methods for electronic medical diagnoses entry and more particularly, to a computerized system and method for rapid data entry of existing or past medical diagnoses.

BACKGROUND OF THE INVENTION

The safe and effective practice of medicine relies greatly upon a physician's obtaining accurate and complete medical records for a patient who is to undergo treatment. Typically, medical records consist of multiple paper forms, physician's notes, test and diagnostic imaging results, and the like. While current medical recordkeeping maintains an effective index to a patient's condition, a patient seeing a new physician, whether a specialist or a new primary care physician, must ensure that his/her medical history, including all past medical diagnoses, is immediately and understandably accessible to the physician. This often requires the transfer of volumes of paper back-and-forth between various medical offices with all of the attendant disadvantages associated with copying, filing and review.

Adoption of electronic medical recordkeeping has not occurred with the same pace and enthusiasm attendant to the adoption of other forms of electronic recordkeeping. Transition performance has been poor for a multitude of reasons, chief of which is the difficulty associated with converting existing medical and patient information to a convenient electronic format.

For example, the most commonly used database (catalog) of medical diagnoses by physicians is termed the International Classification of Disease, $9^{th}$ th Ed. (ICD9) which consists of the detailed list of medical diagnosis which have been extensively compiled over time. The ICD9 is viewed as the gold standard and since it is expressed in a lexicography design for physician use, it generally possesses the descriptive medical rigor necessary for efficient patient management and electronic recordkeeping. Further, it is extensively used as a standard for disease and treatment coding which is necessary for billing in most areas of the United States, particularly in the context of insurance claim processing. However, the ICD9 comprises an estimated 15,000 ICD9 disease codes and searching through them (even electronically) for an appropriate diagnosis code is a tedious and time consuming task for any physician. Additionally, and even more important, there are many conceptually similar ICD9 disease codes which contain no hierarchical links or ontological association to one another, making searches in accordance with disease category or classification inefficient and laborious, if not impracticable.

For example, the disease terms fetal polyhydramnios, intrauterine growth retardation, intrapartum hemorrhage, hyperemesis gravidarum, erythroblastosis fetalis, and hemolytic disease of the newborn all imply that the patient is pregnant, yet none of them contain or refer to the word "pregnancy." Moreover, some are not even classified as diseases of pregnancy. For example, in many ontologies, a hydatiform mole is classified as a malignancy, rather than a disease of pregnancy. Thus, performing a computerized search using an electronic search string including the term "pre*" would fail to return any or all of these diagnoses, depending upon how they were initially categorized and the ontology in which they were categorized. Even when the physician knows the exact disease term desired, computer-based searching can still be inconvenient and inefficient. For example, many medical diseases such as Klippel Feil Syndrome have a non-intuitive spelling, making searching an often frustrating experience. It should be noted that the above limitations are not specific to the ICD9 cataloging system, but to any catalog of medical diseases which might exist (e.g., SnoMed, created by American College of Pathologists).

A typical elderly patient may be taking five different medications, have certain conditions that correspond to five different medical diagnosis, and exhibit an allergic reaction to two different forms of medications. Moreover, a typical physician will very likely have approximately 1,500, or more, patients registered in his/her office practice. Accordingly, this typical individual physician may require electronic data entry for approximately 18,000 data points in order to collect and compile the most basic information about their patients (15,000 patients, each taking five medications on average, and each having five prior medical diagnoses and two allergies, on average). For a typical physician practice group of five or fewer doctors, the cost of manual data entry and upkeep can be financially prohibitive, as well as very demanding of a physician's time, since many physicians would not entrust a non-physician to encode a patient's past medical diagnoses, due to the consequence of inaccurate entry.

While a lay person can easily list their current medications and allergies, e.g., by reading and transcribing a prescription label, very few are able to articulate their specific medical diagnoses. Typically, a patient understands primarily common lay terms which describe the diagnosis he/she may have. For example, a patient may inform the physician that he/she has "an irregular heartbeat" or "heart flutter" but is not able to articulate the accurate medical diagnosis of an "accessory intranodal bypass tract associated with rapid ventricular response". Necessarily, however, an accurate medical diagnosis using rigorous medical terminology is crucial for optimal patient management, as well as computerized medical decision support. Hence, electronic medical records which are to be utilized by physicians ideally necessitate accurate diagnoses using specific and detailed medical terminology such as that found in the ICD9 vocabulary.

Accordingly, there is a strong need for both systems and methods by which information relating to any particular patient's current medications, conditions, allergies, and the like, to be rapidly entered into an electronic database with minimal cost and minimal time commitment on the part of a physician. Such systems and methods should be simple, cost-effective and allow for participation and/or use by lay persons such as office clerical staff and a patient themselves.

SUMMARY OF THE INVENTION

In one particular aspect, the invention might be considered a method for identifying a clinically relevant diagnosis from ancillary input data such as the name or names of a patient's medications. The method comprises defining a database which is accessible by an electronic data input and processing device such as a hand-held, laptop or desktop-type computer or PDA. A multiplicity of indication terms are established within the database, the terms describing a medical or physiological condition in accordance with a standardized usage. A multiplicity of clinically relevant diagnoses are established within the database, the diagnoses each associated to a particular one of the multiplicity of indication terms. Each of the multiplicity of indication terms is linked to a normalized medication index and particular ones of the indication terms are identified upon input of a particular medication to the electronic data input and processing device. Upon identification, the particular ones of the indication terms are displayed as an indication set by the device.

Suitably, a particular indication is selected from the indication set and particular ones of the clinically relevant diagnoses are displayed as a specific diagnosis set by the device upon selection of a particular indication by a physician. The particular clinically relevant diagnosis selected from the specific diagnosis set is entered into an electronic patient medical record.

In a further aspect of the invention, the normalized medication index comprises a database collection of medications, each medication identified by a tradename, each medication further identified by a generic name, the tradenames and generic names are associated to one another by database pointers such that any medication entry terminology returns a medication's generic name as the normalized medication index. Each of the multiplicity of indication terms is linked to a normalized medication index in accordance with an administratively authorized medication to indication usage. In particular, the administratively authorized medication to indication usage is an FDA approved usage. Additionally, particular ones of the multiplicity of indication terms are linked to a normalized medication index in accordance with a recognized common usage without regard for administrative authorization.

A beneficial feature of the present invention is that the clinically relevant diagnoses are selected from a recognized standardized medical reference of clinically relevant diagnoses such as the ICD9. Advantageously, ICD9 terminology normalizes diagnosis terminology across the entire community of users. Further the ICD9 disease codes are suitable for automatic entry into an electronic patient medical record.

In an additional aspect, the present invention comprises a system for extracting a clinically relevant diagnosis from ancillary input data such as a medication. The system includes an electronic data input and processing device including at least a display and means for inputting and further incorporates a database accessible by the electronic data input and processing device. The database is structured to include a multiplicity of indications, each indication describing a medical or physiological condition in accordance with a standardized usage. A multiplicity of clinically relevant diagnoses are each associated to a particular one of the multiplicity of indications, and a multiplicity of normalized medication indices are each linked to selected ones of the multiplicity of indications.

A diagnosis extraction application program is hosted on the electronic data input and processing device, with particular ones of the indications being automatically identified upon input of a particular medication to the electronic data input and processing device. Once identified, the indications are displayed to a user as an indication set. A particular indication is selected from the indication set, the application automatically identifying particular ones of the clinically relevant diagnoses upon selection of a particular indication, and displaying the relevant diagnoses to a user as a specific diagnosis set.

Functionally, the invention is characterized as a method for defining clinically relevant diagnoses from ancillary input data, and comprises the steps of entering a medication identification into an electronic data input and processing device, normalizing the medication identification into a standardized medication index, and reverse indexing the normalized standardized medication index to a first set of relevant ones of indications identified to the medication index. The first set of selected ones of indications are displayed to a user who selects a particular one of the first set of indications. The selected one of the first set of indications is concept matched to a second set of specific diagnoses, where each specific diagnosis identified to the selected indication. The second set of specific diagnoses is displayed to the user who selects a particular one of the second set of specific diagnoses as the clinically relevant diagnosis.

In a further aspect of the present invention, the normalization step further comprises mapping a medication tradename to the medication's generic description, such that medication identification entry is made without regard to a medication label. The concept matching step further comprises establishing a categorical collection of clinically meaningful groups, associating recognized indication terminology with each group and associating specific diagnoses to a particular group in accordance with a conceptual congruence between the specific diagnosis and the group. The clinically meaningful groups comprise pathologically related classifications and consist of viral infections, bacteriological infections, structural defects, metabolic defects, genetic defects, and autoimmune defects.

DESCRIPTION OF THE DRAWINGS

These and other features, aspects and advantages of the present invention will be more fully understood when considered in connection with the following specification, appended claims and accompanying drawings wherein:

FIG. 1 is a simplified, semi-schematic illustration of an exemplary extraction of a specific diagnosis from a normalized medication entry, in accordance with practice of the present invention;

FIG. 2 is an exemplary database relation diagram depicting mapping between a medication tradename, medication manufacturer and medication generic or chemical name;

FIG. 3 is a simplified, semi-schematic illustration depicting entry of a specific diagnosis from a normalized medication entry into a medical record, in accordance with practice of the present invention;

FIG. 4 is a simplified, semi-schematic illustration of an additional embodiment of an exemplary extraction of a specific diagnosis from a normalized medication entry, in accordance with practice of the present invention;

FIG. 5 is a simplified, semi-schematic illustration depicting entry of a general indication from a normalized medication entry into a medical record, in accordance with practice of the present invention; and FIG. 6 is a simplified, semi-schematic illustration depicting entry of a specific diagnosis from a general indication entry into a medical record, in accordance with practice of the present invention.

DESCRIPTION OF THE INVENTION

The present invention relates to a system and methodology by which data fields relating to a particular patient's current medications and/or allergies allow their past medical diagnoses to be rapidly entered into an electronic database with minimal cost and minimal time commitment on the part of the physician. Data entry is performed in accordance with a computerized reverse-indexing system that utilizes an intermediate, medication indications database, combined with concept-matched specific diagnoses extracted from a conceptual database, where the specific diagnoses are identified in accordance with detailed medical terminology such as might be expressed in the ICD9 or some other medically robust catalog of medical disease classifications. In addition to providing enhanced efficiency, the accuracy and rigor of standard medical terminology, particularly with regard to a patient's past medical diagnoses, is preserved.

The methodology, in accordance with the invention, utilizes an initial data entry of only current medications and known allergic responses, ideally made either by the patient themselves, or by a medical assistant (to expedite clinical workflow) in consultation with the patient. However, a physician is necessarily also enabled to do so. This initial data set of medications and/or known allergic responses, is then electronically processed by a computer, or other purpose-built processing engine, and the list of medications and/or known allergic reactions, is reverse-indexed using a concept-matching intermediate database, to a set of macro diagnoses. In the context of the invention, a macro diagnosis represents one of a multiplicity of broad conceptual reasons why the medication might have been prescribed. A conceptual macro diagnosis is selected from the presentation, and once selected, a specific set of discrete diagnoses is then presented, each associated to the selected conceptual macro diagnosis, with sufficient rigor of terminology, such as might be found in the ICD9 database.

Utilizing this system and method, a physician is able to view a narrowed and focused set of macro diagnoses, followed by a discrete, rigorously descriptive, set of ICD9 diagnoses, in order to rapidly complete entry of a patient's exact medical diagnosis. Occasionally, a macro diagnosis in the intermediate table will have the same terminology as the exact medical diagnosis required. For example, the drug azidothymidine (AZT) is only used for the treatment of HIV (AIDS). In this particular case, the single macro diagnosis is equivalent to the exact rigorous diagnosis and the rigorous diagnosis is returned automatically without the requirement of an additional selection step. Conversely, in the case of a medication such as atenolol, there may be several conceptual macro diagnoses for which it might be prescribed, including tremor hypertension, migraines, and glaucoma. If hypertension was indicated by the patient as the reason for taking the medication and thus selected as the macro diagnosis, the physician might be presented with a more focused list of discrete diagnoses to choose from. In the exemplary embodiment, for example, selecting hypertension from the intermediate indications list would cause a set of specific diagnoses, each associated to the conceptual indication of hypertension, to be presented to the physician for selection. Such further choices might include malignant hypertension, essential hypertension, secondary hypertension, pheochromocytoma, renovascular hypertension, etc., each of which has a specific ICD9 diagnosis code. In the exemplary embodiment, the specific diagnosis might be selected as "essential hypertension" which corresponds to an ICD9 code of 401.9 (an exact ICD9 match).

In the initial portion of the methodology of the invention, as depicted in the exemplary embodiment of FIG. 1, a patient (or a physician or medical assistant) enters any and all of the mediations that are currently being taken by the patient into a computer system, either through direct text entry or by using a scannable paper form which converts data into an electronic format (a scannable bubble sheet, for example). Since medications are often identified by multiple names, e.g., different trade names and a generic name, the medication input data is normalized to account for various differing identifying names for the same medication. Normalization is the terminology used to describe the accounting process which takes place upon data entry of any one of an item's trade names, chemical description or generic name.

For example, atenolol, a synthetic beta-selective adrenal receptor blocking agent, might be known by the trade name Tenormin, or by its chemical description (atenolol) which is also its generic name. Data normalization ensures that however the particular medication is described, it is related to a particular identifying index which is generally based upon both the chemical name and the manufacturer, who may use different carrier vehicles that convey additional physiological properties that are significant clinically. In the example of FIG. 1, a search for a particular drug may be undertaken in accord with well known electronic search principles. Searching may be done in the context of "all drugs" contained within the database, or in the context of an alphabetical listing. An alphabetical search string (preferably two or more letters) returns a set of corresponding database entries, initiated with the string, from which a user may select the most appropriate entry.

In the example of FIG. 1, the user has elected to search by "all drugs" that begin with the search string "ATE". This search procedure has returned six possible entries that satisfy the search criteria; Atel, Atenoblok-Co, Atenolol, Atenolol w/Chlorthalidone, Atenolol:Chlorthalidone, and Atensin. This is a particularly useful search procedure, especially where the name of the drug (whether generic or trade) is known. In cases where the tradename is known, the search may be performed in accord with that trade terminology, by selecting perhaps "tradename" from the "search by" field rather than "all drugs". Inputting Tenormin, or "TEN" into the search string field, would return an entry for Tenormin (among others) that is associated to the generic name Atenolol by the normalization database.

Specifically, and as indicated in the exemplary embodiment of FIG. 2, a normalization database is a many-to-many relational structure, with three significant groupings, each of which reference the others through multiple relationships. The three basic groups include a trade name grouping, a manufacturer grouping and a chemical composition (generic name) grouping. Elements in each of the three groupings are related to one another by pointers that might associate the trade name Tenormin with the generic medication atenolol. In the exemplary embodiment of FIG. 2, for example, the generic name portion might include a listing for the term ibuprofen which is associated with various manufacturers such as Bayer, Johnson & Johnson, and the like, each of which might market the product under various trade names such as Motrin, for example. Thus, ibuprofen is associated to various trade names by pointers directed to the manufacturer portion of the database and thence to the trade name portion.

Thus, it can be understood that a particular manufacturer might market a particular generic medication under various trade names, each of which might use a different carrier vehicle for the generic medication. Additionally, each manufacturer is associated to several different generic medications and to the trade names associated with those various generic medications. Accordingly, the data normalization database ensures that no matter how a particular medication is input, the input data is associated to a particular identifying index, typically the generic name or chemical description of the medication. In this regard, it should be noted that the database need not include any manufacturer information portion in order to retain its functionality. As those having skill in the art of database design will immediately recognize, the database might be suitably constructed with pointers directly linking a medication's generic or chemical name to each of a collection of trade names that contain the generic chemical agent. Including a manufacturer designation is for purposes of convenience, and to allow expansion of the functionality of the invention to include contraindication alerts based upon carrier vehicle incompatibility, for example.

Generic agent name to trade name linkages may also be made through a classification index, for example. Penicillin and amoxycillin both belong to the class of beta-lactam antibiotics. These antibiotics and their respective trade names can be cross-linked to one another by virtue of their joint membership in the class of beta-lactam antibiotics, with database pointers directed in both directions. Thus, entry of a particular trade name returns either a generic/chemical name, an effectivity classification name, a set of generic/chemical names of agents belonging to the classification, or any desired combination of the foregoing.

In a further extension of the methodology, allergies and allergic reactions to particular medications, drugs, therapies, or the like, are treated in a substantially similar fashion, with a drug allergy, e.g. to penicillin, being identified as an allergic reaction to a class of beta-Lactam antibiotics. In this particular situation, an additional database portion, a medication classification portion, is included in the normalization database and functions to assign each of the generic (chemical) name medications to a particular classification. Accordingly, an indication of penicillin hypersensitivity would suggest a sensitivity to other medications in the beta-Lactam antibiotic classification. Thus, penicillin hypersensitivity would be associated amoxycillin, as well.

Once a particular patient's medication (and allergy) program have been entered, the normalized data is matched to a number of possible indications (macro diagnoses) that are associated with any particular medication in a process termed "reverse-indexing". As will be understood by those having skill in the art, drugs, medications and therapies all must be approved by the U.S. Food and Drug Administration (FDA) for use as treatments for particular indications. For example, amoxicillin is considered a drug of choice for the treatment of acute sinusitis, acute otitis media, and of acute exacerbations of chronic bronchitis. Amoxyicllin is also suitable for treatment of streptococcal pharyngitis, and is important as an alternative to co-trimoxazole for uncomplicated infections of the urinary tract (particularly as a single dose for non-pregnant women).

In this particular example, the National Drug Code (NDC), a unique catalog of every medication which is FDA-approved in the United States, combined with other data ubiquitously available from the FDA, is able to provide the basis for an FDA-approved indications database, with various drug formulary entries associated with their corresponding indications. Conventionally, physicians select a medication on the basis of an observed indication, but in the context of the invention, medications identify their corresponding indications which are presented to the physician as a reverse-index of discrete choices of macro diagnoses.

Indications or macro diagnoses are a collection of relatively descriptive terms, typically cast in lay person's language, which describe a particular disease or condition without regard to precise medical terminology. For example, and in accordance with the exemplary embodiment of FIG. 1, indications for atenolol include acute myocardial infarction, angina, ethanol withdrawal, hypertension, migraine prophylaxis, myocardial infarction prophylaxis paroxysmal supraventricular tachycardia, and unstabel angina. If a patient is taking atenolol, the physician will be presented with these possible indications (macro diagnoses) from the indications in that database, as a result of an "atenolol" entry into the system.

Indications are presented on a screen segment (as shown in FIG. 1) that is invoked by selection of "Atenolol" on the entry list of input medications. As will be understood by those having skill in the art, only those indications associated to Atenolol are presented on the indications screen. Presented with these indication choices on a computer monitor screen or the display of a hand-held or tablet-type computer, a physician is able to quickly query a patient to determine whether he/she is taking the particular mediation for any one of the presented indications. The primary indication is then selected by the physician for incorporation into the patient's current medical history, as described further below. In the exemplary embodiment of FIG. 1, for example, the physician has indicated the primary indication as "Unstable Angina".

Generally, a patient will know whether he/she is taking atenolol for the treatment of ethanol withdrawal, angina or hypertension, for example, and would be able to so indicate to the physician. Also, in many instances, the patient will be an established patient and the physician will either have the patient's chart available for reference or might have a referral note from another physician, in which case the M.D. knows what the indication is for a given mediation (even if the patient themselves may not be aware). Indeed, the purpose of reverse-indexing is to rapidly present a concise list of the most likely diagnoses for which a medication might be provided, thereby reducing the number of diagnostic choices and eliminating the need for the physician to query a massive (e.g., ICD9) database of all possible diagnoses, as well as trying to determine how the disease might be classified. The objective of the invention is to greatly expedite the data entry process required to encode a patient's specific current medical diagnosis in a highly granular and clinically rigorous form (e.g., secondary hypertension due to renovascular stenosis, as opposed to merely 'high blood pressure').

In this regard, an indications (macro diagnoses) database is a highly useful tool because it gives the physician a list of indications in lay person's terminology that can be discussed with the patient. Necessarily, many of the clinically rigorous diagnoses can be classified into a particular indications classification. As will be described in greater detail below, various medical terms are arranged into clinically meaningful groups, each of which might be subsumed under the rubric of a particular indications (macro diagnosis) term. In the exemplary embodiment of FIG. 1, presuming that the patient identifies unstable angina as the condition for which they are taking atenolol, the physician need only mark the "unstable angina" indication for further analysis. In the context of an electronic system, implementing the invention, marking might be performed by tapping the display screen portion which displays the indication with a touch pen, or by selecting the indication with a moveable cursor, or the like. Those having familiarity with computer systems in general will appreciate that all that is required for marking is some means for identifying the indication text "hypertension" as the particular indication (macro diagnosis) for which the medication is being taken.

Once a likely indication has been identified, the physician must now associate the indication with a set of specific diagnoses that are identified in accordance with detailed medical terminology, where the diagnoses are hierarchically and/or ontologically associated to the respective indication. In other words, indications are expressed in what might be thought of as layman's terminology which, although informative, often are clinically of limited utility at best because they are not granular enough in nature. The physician needs to extract a diagnosis in more technical terminology from a subsequent database in which specific and exact diagnoses are concept-matched to particular indications.

Prior to discussing the structure and use of a conceptual database, it should be noted that the indications database uses existing "catalogs" of indications as a foundation. Most of the existing catalogs, such as the NDC, relate to common indications which are approved by the FDA. However, physicians understand that certain medications may be used for "real world" indications that might not involve FDA approval. Notwithstanding their unapproved nature, real world indications are also incorporated in the indications database by mass solicitation, database sharing between physicians, and other forms of information acquisition that are well known to those having skill in the art. The indications (macro diagnoses) database is therefore a composite of FDA-approved and non-FDA approved indications, thereby offering a more complete and robust set of matching principles for any particular drug, medication, therapy, or the like.

Further, it should be understood that the vast majority of patients who visit a physician are only taking a limited number of medications (from four to ten medications, on average). Each of these medications are typically associated with approximately five different indications, on average. Thus, the database pointer system can be relatively simple and database results can be easily displayed on a simple handheld or laptop-type information retrieval and processing device.

A conceptual database (also termed a specific diagnosis database) arranges specific diagnoses, in strict medical terms, into clinically meaningful groups by classifying and unifying diseases into common pathologically related sets that each have a unifying medical cause (mechanism) at a physiological level. For example, the conceptual database might be structured to classify diseases in accordance with six pathologically related groups; viral infections, bacteriological infections, structural defects, metabolic defects, genetic defects, and autoimmune defects. Within each of these groups, discrete ICD9 diagnoses are mapped to one or more terms that might be commonly used as an indication for which a particular medication is prescribed.

As will be understood, the pathologically-related groups are further subdivided into various classifications, each of which are associated with certain terms that are commonly used to describe a particular indication, as might be defined by the FDA, or by the medical community in general. Thus, in a particular embodiment, the methodology might be viewed by either classifying an ontology/hierarchy in terms of indications, or by classifying indications in terms of an ontology/hierarchy, with the unifying principle being particular chosen terminology or terms that have meaning, not only for the physician, but also for the patient. Terminology mapping thus allows for data mapping between specific medications and specific diagnoses through a descriptive association, termed an indication.

Notwithstanding the foregoing, it should be understood that many indications may be directly associated to an ICD9 code, for example, and may therefore be directly entered without further analysis. The exemplary embodiment of FIG. 3 depicts a screen shot of an electronic patient record which is organized to depict the patient's past medical history, past surgical history, medications and allergies, in separate window portions. Following the example of FIG. 1, an entry has been made for "Unstable Angina" in the patient's past medical history record. Also, an entry for Atenolol appears in the patient's medications listing, with "unstable Angina" being given as the indication for which the medication is being taken. Each of the patient's diagnoses is associated to its corresponding ICD9 code. For example, Cystitis has an ICD9 code of 595.9; zinc deficiency has a code of 985.8. It will be seen that Unstable Angina has a code of 411.1.

In a further example, and in connection with the exemplary embodiment of FIG. 4, a particular indication might have a number of clinically relevant diagnoses associated with it, each of which must be considered by a physician when defining a patient's medical history. The term "Diabetes Mellitus" for example, might relate to several specific diagnoses, some with neurological implications and some with circulatory disorder implications. In the exemplary embodiment of FIG. 4, a patient is taking the drug Avandia. Avandia is a tradename for rosiglitazone maleate, one of a class of thiazolidinediones by GlaxoSmithKline, useful in the treatment of class 2 diabetes. Avandia was selected by inputting the search string "ava". The normalization database contains pointers that associate Avandia with rosiglitazone maleate and the class of thiazolidinediones. Each of these terms in the normalization database points back to an indications entry of "Diabetes Mellitus, so that this indication is returned, no matter whether the drug was entered as Avandia, or one of its analogs.

Avandia was selected from the search return list, which, in turn, invokes the possible indications list, which includes all indications associated to the chosen drug. In the embodiment of FIG. 4, Diabetes Mellitus is the only indication found, and is selected as the primary indication by the user. Diabetes Mellitus now becomes an entry in the patient's medical history, as shown in the exemplary screen shot of FIG. 5.

In FIG. 5, Diabetes Mellitus has been added to the diagnosis list of FIG. 3, but it should be noted that there is no specific ICD9 code associated with diabetes Mellitus. This is indicated by a 000.0 entry in the ICD9 code section suggesting that further analysis is required to develop a clinically sufficient diagnosis. When the conceptual database is constructed, the indication diabetes mellitus is associated to a number of clinically relevant diagnoses, including various forms of type I diabetes and various forms of type II diabetes, each with their own ICD9 code entry. As a physician selects the "Diabetes Mellitus" entry from the patient's medical history portion in FIG. 5, a separate screen, illustrated in the example of FIG. 6, depicts a further list of rigorous diagnoses associated with the indications term diabetes mellitus, along with each diagnoses' associated ICD9 code. The physician is then able to select the most clinically relevant specific diagnosis from the list and add the diagnosis to the patient's medical history records. This gives the physician the opportunity to review a relatively complete set of diagnoses, in proper medical terminology, in order to determine which one of the set pertains to the specific patient at issue.

In the context of the conceptual (specific diagnosis) database as a whole, it should be understood that it can be integrated with the indications database, such that only the display and selection functions are multi-step. The indications and conceptual database are structured with specific disease codes pointing to imposed standardized indications terminology, with both the indications and diseases pointing to a normalized medication index, such as a particular generic or chemical name. For example, "benign essential hypertension" would point to both the indication "hypertension" and the medication atenolol, with atenolol also pointed to by the indication "tremor" and the specific diagnosis "Sydenham's Chorea". "Hypertension" might also be associated with the medication propanolol which is, in turn, associated to a different specific hypertension diagnosis.

Once a physician is presented with a suitable set of specific diagnoses from the conceptual (specific diagnosis) database, the physician is able to choose the proper diagnosis, either in consultation with the patient, or from their recollection or records, and add that diagnosis to a computerized patient history rapidly and accurately, without the extensive searching that would otherwise be required. After selecting an indication (a macro diagnosis) that is not sufficiently rigorous in itself, the physician is presented with a further list of specific diagnoses in rigorous medical jargon, and the selection process becomes relatively simple and straightforward. A physician may now select the diagnosis from a short list of anywhere from three to about ten items, as opposed to attempting to select a diagnosis from a list of tens of thousands of items such as comprise the ICD9.

Further, selecting a specific diagnosis requires only that a physician once again mark (by tapping, clicking, or otherwise indicating) the specific diagnosis, in order to enter that particular diagnosis, along with its ICD9 billing code, for example, into the patient's electronic medical records. Since the database is electronic, and is available for downloading and sharing among the entire medical community, the indications, as well as the specific diagnoses, form a standardized terminology set which is uniform across the entire community. By contrast, ICD9 information is often classified in a non-clinical sense and is expressed in a manner that is difficult to spell correctly, resulting in difficult and labor intensive searches to acquire a result. Since the present methodology defines a database in which the terms are uniform and term selection involve only electronic indexing from a hierarchical presentation structure, the system and method of the present invention effectively precludes the kinds of mistakes and omissions that are attendant to the current manual data collection entry and searching process.

In accordance with the invention, in a general sense, the methodology might be thought of as involving development of an intermediate indications diagnosis from a medication index, using the "sum of the meds" as an input filter. Input medications are normalized, typically to a generic or chemical name terminology, such that a specific result is returned for each medication, regardless of how that medication might be identified in the input process. Each of that medication's synonyms, tradenames, or chemical designations are associated to a corresponding indication or indications. Intermediate indications diagnosis development returns a short list of possible indications consistent with the medication or medications, with the indications (macro diagnoses) expressed in common, functional language, or where appropriate, as a sufficient diagnosis indication. Each macro diagnosis (indication) is reverse-indexed to medications in accordance with FDA approvals and common non-FDA usages.

Once the input meds are normalized and reverse-indexed to a macro diagnosis or indication, a macro diagnosis or indication is chosen. The chosen macro diagnosis or indication is concept-matched to a list of rigorous diagnoses in order to develop a proper diagnosis in clinically meaningful terms from a concept-mapped portion of a database. The concept-mapped portion is developed by grouping medical terms into clinically meaningful groups and developing pointers between and among the members of those groups so as to map identified diseases (rigorous diagnoses) to terminology from a developed indications taxonomy, itself developed by forming a composite of FDA-approved and non-FDA approved indications with respect to particular medications.

In terms of its systematic implementation, the present invention suitably comprises a normalization, indication and concept-mapped database, hosted on a computer or data processing system of suitable type. The database is accessible to a hand-held, laptop-type or desktop-type computer display for access by a physician or clinical worker. In addition to being hosted on a local data processing machine, the database is contemplated as being maintained in a centralized data processing server implementation, such that it is accessible through a local or wide area network for download by a physician or practice group. Maintaining the database in a centralized location allows database terminology to be maintained on a more uniform basis, thereby minimizing the present-day confusion generated by inconsistent terminology for both indications and clinically relevant diagnoses. In a manner well understood by those having skill in the art, database contents are also uploadable to the centralized server so that additions and embellishments may be provided to the centralized system by physicians that may have discovered an additional indications usage for a particular medication and who wishes to share this information with the medical community at large.

In addition to being a self-contained exact diagnosis extraction device, the system of the present invention also incorporates an interface to any one of a number of commercially or conventionally available electronic medical record-keeping applications, such that as an exact diagnosis is extracted, the exact diagnosis is automatically ported to the appropriate input port of the medical records program. In particular, the data entry application, and its associated database, are implemented as an application software program that is written with the requisite I/O "hooks", such that it can be incorporated as an "applet" or "servelet" in a medical recordkeeping program. As patient information is added in conventional fashion, the medical record program invokes the application of the invention as soon as the physician reaches the "medications", "indications", or "diagnoses" portions of the recordkeeping program input.

Accordingly, the present invention can be understood as defining a particular system and methodology by which a patient's existing medical diagnoses can be rapidly entered into an electronic recordkeeping database with minimal cost and minimal time commitment on the part of a physician. The system utilizes a computerized reverse-indexing system implementing an intermediate, medication/indications database combined with concept matching in order to derive specific, clinically relevant diagnoses on the basis of known existing medications, which can be entered by either a patient, lay person, medical assistant or physician.

While the above specification has shown, described and identified several novel features of the invention, as applied to various exemplary and illustrated embodiments, it will be understood that the embodiments are for purposes of illustration and ease of description only. Various omissions, substitutions and changes in the form and details of the exemplary embodiments may be made by those skilled in the art without departing from the scope and spirit of the present invention.

Accordingly, the invention is not contemplated as being limited to the described, exemplary and illustrated embodiments, but are rather defined by the scope of the appended claims.

The invention claimed is:

1. A method for identifying a clinically relevant diagnosis from ancillary input data, the method comprising:
   defining a database, the database accessible by an electronic data input and processing device;
   storing a multiplicity of indication terms within the database, each indication term describing a medical or physiological condition in accordance with a standardized usage;
   storing a multiplicity of clinically relevant diagnoses within the database, each diagnosis is associated to one or more of the multiplicity of indication terms, wherein each diagnosis is a disease or condition specified with detailed medical terminology;
   linking, in the database, each of the indication terms to a normalized medication index wherein a chemical name, trade name and a manufacturer name of a medication are associated with one or more indication terms;
   receiving an input of one of a chemical name, trade name and a manufacturer name of a medication;
   automatically identifying, based on multiplicity of indication terms in the database and linked normalized medication index, one or more of the indication terms upon input of the medication to the electronic data input and processing device, wherein the identified one or more indication terms are displayed as an indication set by the device; and
   selecting one of the indication terms from the indication set; and
   automatically identifying one or more of the clinically relevant diagnoses upon selection of the indication term based on the association of one or more of the multiplicity of indication terms with each diagnosis, wherein the identified one or more clinically relevant diagnoses are displayed as a specific diagnosis set by the device.

2. The method according to claim 1, further comprising:
   selecting one of the clinically relevant diagnosis from the specific diagnosis set; and entering the selected diagnosis into an electronic patient medical record.

3. The method according to claim 2, wherein the clinically relevant diagnoses are selected from a recognized standardized medical reference of clinically relevant diagnoses.

4. The method according to claim 3, wherein the recognized standardized medical reference comprises the ICD9.

5. The method according to claim 4, wherein the ICD9 further comprises disease codes that are automatically entered into an electronic patient medical record.

6. The method according to claim 1, wherein the normalized medication index comprises a database collection of medications, each medication identified by a tradename, each medication further identified by a generic name, the tradenames and generic names associated to one another such that any medication entry terminology returns a medication's generic name as the normalized medication index.

7. The method according to claim 6, wherein each of the multiplicity of indication terms is linked to a normalized medication index in accordance with an administratively authorized medication to indication usage.

8. The method according to claim 7, wherein one or more of the multiplicity of indication terms are linked to a normalized medication index in accordance with a recognized common usage without regard for administrative authorization.

9. A system for extracting a clinically relevant diagnosis from ancillary input data, the system comprising:
   an electronic data input and processing device including at least a display and means for inputting;
   a database accessible by the electronic data input and processing device, the database further comprising a multiplicity of indications wherein each indication describes a medical or physiological condition in accordance with a standardized usage, a multiplicity of clinically relevant diagnoses, the diagnoses each associated to one or more of the multiplicity of indications; and a multiplicity of normalized medication indices, each index having a chemical name, trade name and a manufacturer name of a medication linked to one or more of the multiplicity of indications; and
   a diagnosis extraction application, hosted on the electronic data input and processing device, wherein one or more of the indications are automatically identified upon input of a medication to the electronic data input and processing device, and wherein the one or more of the indications are displayed to a user as an indication set and wherein one or more of the clinically relevant diagnoses are automatically identifying upon selection of the selected indication based on the association of one or more of the multiplicity of indication terms with each diagnosis wherein the one or more of the clinically relevant diagnoses are displayed to a user as a specific diagnosis set.

10. The system according to claim 9, further comprising an electronic patient medical record keeping application, wherein a clinically relevant diagnosis selected from the specific diagnosis set is automatically entered into an electronic patient medical record.

11. The system according to claim 10, the normalized medication indices further comprising:
   a database collection of medication tradenames;
   a database collection of medication generic names; and
   a defined pointer set, wherein the tradenames and generic names are associated to one another through pointers such that any medication entry terminology returns a medication's generic name as the normalized medication index.

12. The system according to claim 11, wherein each of the multiplicity of indications is linked to a normalized medication index in accordance with an administratively authorized medication to indication usage.

13. The system according to claim 12, wherein one or more of the multiplicity of indications are linked to a normalized medication index in accordance with a recognized common usage without regard for administrative authorization.

14. The system according to claim 13, wherein the clinically relevant diagnoses are selected from a recognized standardized medical reference of clinically relevant diagnoses.

15. The system according to claim 14, wherein the recognized standardized medical reference comprises the ICD9.

16. The system according to claim 15, wherein the ICD9 further comprises disease codes that are automatically entered into an electronic patient medical record.

* * * * *